(12) United States Patent
Tomatsu et al.

(10) Patent No.: US 9,131,840 B2
(45) Date of Patent: Sep. 15, 2015

(54) OPTICAL COHERENCE TOMOGRAPHIC IMAGING APPARATUS AND TOMOGRAPHIC IMAGING METHOD

(75) Inventors: Nobuhiro Tomatsu, Yokohama (JP); Futoshi Hirose, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 159 days.

(21) Appl. No.: 13/259,534

(22) PCT Filed: May 13, 2010

(86) PCT No.: PCT/JP2010/058493
§ 371 (c)(1),
(2), (4) Date: Sep. 23, 2011

(87) PCT Pub. No.: WO2010/134564
PCT Pub. Date: Nov. 25, 2010

(65) Prior Publication Data
US 2012/0026464 A1   Feb. 2, 2012

(30) Foreign Application Priority Data

May 22, 2009   (JP) ................................. 2009-123920

(51) Int. Cl.
*A61B 3/10* (2006.01)
*A61B 3/14* (2006.01)

(52) U.S. Cl.
CPC ..................... *A61B 3/102* (2013.01)

(58) Field of Classification Search
USPC .................. 351/200–208, 221–225, 245–246; 356/479, 477, 497; 359/349, 489.09, 359/583, 626–639
See application file for complete search history.

(56) References Cited

U.S. PATENT DOCUMENTS

| 7,830,524 | B2 | 11/2010 | Teramura et al. |
| 7,982,881 | B2 | 7/2011 | Fercher et al. |
| 8,437,008 | B2 | 5/2013 | Fercher et al. |
| 2004/0036838 | A1 | 2/2004 | Podoleanu et al. |
| 2005/0104136 | A1* | 5/2005 | Edwards et al. ............... 257/400 |
| 2005/0190372 | A1 | 9/2005 | Dogariu |
| 2007/0159595 | A1 | 7/2007 | Fukuma et al. |
| 2007/0229939 | A1* | 10/2007 | Brown et al. ............... 359/341.1 |
| 2008/0304543 | A1* | 12/2008 | Abe et al. ..................... 374/120 |
| 2009/0091766 | A1* | 4/2009 | Hirose ........................... 356/479 |
| 2010/0046338 | A1* | 2/2010 | Saito et al. .................. 369/47.15 |

FOREIGN PATENT DOCUMENTS

JP   2007-151631 A   6/2007
JP   2007-181631 A   7/2007

(Continued)

*Primary Examiner* — Stephone B Allen
*Assistant Examiner* — Brandi Thomas
(74) *Attorney, Agent, or Firm* — Fitzpatrick, Cella, Harper & Scinto (57) ABSTRACT

An imaging apparatus that irradiates an object with a first measuring beam and a second measuring beam that differ from each other in a center wavelength, and acquires an image of the object using returning light from the object. A first adjustment unit adjusts a focusing position of the first measuring beam in a depth direction. A second adjustment unit adjusts a focusing position of the second measuring beam in the depth direction. A controlling unit controls at least one of the first adjustment unit and the second adjustment unit such that the focusing position of the first measuring beam and the focusing position of the second measuring beam are at different positions in the depth direction.

32 Claims, 7 Drawing Sheets

(56) References Cited

FOREIGN PATENT DOCUMENTS

| | | |
|---|---|---|
| JP | 2008-128708 A | 6/2008 |
| JP | 2009-518088 A | 5/2009 |
| WO | 2006-020408 A | 2/2006 |
| WO | 2009-061756 A | 5/2009 |

\* cited by examiner

OPTICAL COHERENCE TOMOGRAPHIC IMAGING APPARATUS AND TOMOGRAPHIC IMAGING METHOD

TECHNICAL FIELD

The present invention relates to an optical coherence tomographic imaging apparatus and tomographic imaging method, and more particularly, to an optical coherence tomographic imaging apparatus and tomographic imaging method which are used for ophthalmologic diagnosis.

BACKGROUND ART

Currently, an apparatus based on optical coherence tomography (OCT) (i.e., an optical coherence tomographic imaging apparatus; hereinafter referred to as an OCT apparatus) which uses a low coherence interferometer can obtain tomography images of a specimen (test object) at high resolution. The OCT apparatus is becoming indispensable as an ophthalmologic apparatus for specialized retinal outpatient clinics. Also, various developments are being carried out toward application to endoscopy.

By irradiating a test object with measuring beam which is a low coherence light, the OCT apparatus can measure backscatter from the test object at high sensitivity using an interferometer.

Also, by scanning the test object with the measuring beam, the OCT apparatus can obtain tomography images at high resolution.

The OCT apparatus can also acquire tomography images of the retina in the ocular fundus of the eye under examination at high resolution, and is widely used for ophthalmologic diagnosis of the retina.

In particular, with the advent of the OCT apparatus, tomography images of the retina can now be acquired at high resolution, enabling detection of small lesions which have been difficult to find by conventional diagnosis procedures.

Therefore, the OCT apparatus is expected to facilitate early detection of ocular fundus diseases, and various developments are being carried out.

The OCT apparatus, when used in ophthalmologic diagnosis of the retina, uses near-infrared light, which is poorly absorbed by water. Moreover, shorter wavelengths which are more poorly absorbed are favored, and near-infrared light with a center wavelength of around 800 nm is widely used conventionally. The near-infrared light around 800 nm is strongly absorbed or scattered in deep layers of the retina. This makes it difficult for light to reach the choroid, raising a problem in that it is difficult to acquire tomography images of the deep layers.

To deal with this problem, Japanese Patent Application Laid-Open No. 2007-181631 discloses an OCT apparatus which uses a wavelength longer than 800 nm with a larger penetration depth to carry out imaging at deep sites near the choroid in the back of the eye. The OCT apparatus disclosed in Japanese Patent Application Laid-Open No. 2007-181631 is an ocular fundus imaging apparatus which performs OCT using a light source with a wavelength of 1000 nm to 1100 nm to image deep layers of the retina including the choroid and sclera.

Also, Japanese Patent Application Laid-Open No. 2007-151631 discloses ophthalmologic radiography apparatus which uses a light source with a wavelength in the 1,500 nm band in addition to light in the 800 nm band and changes focusing position with the wavelength to increase depth of focus. The ophthalmologic radiography apparatus makes lights from the two light sources enter a test object alternately, combines tomography images obtained alternately, and thereby obtains a tomography image with a wide range.

DISCLOSURE OF THE INVENTION

The apparatus disclosed in Japanese Patent Application Laid-Open No. 2007-181631 is equipped with only one light source, and cannot use multiple lights with different wavelengths simultaneously. Consequently, the apparatus has a problem. Namely, the apparatus cannot carry out imaging near the surface at high resolution although it can carry out imaging deep in the back of the eye.

Also, the technique disclosed in Japanese Patent Application Laid-Open No. 2007-151631 is equipped with the low coherence light source in the 800 nm band and low coherence light source in the 1,500 nm band, and can virtually increase depth of focus by offsetting the focusing positions of the two lights with different wavelengths from each other using chromatic aberration. However, the technique, which carries out imaging by switching between the two lights with different wavelengths, cannot measure the same part simultaneously. Also, since the technique offsets the focusing positions using only chromatic aberration, influence of the visibility of the eye cannot be eliminated.

In view of the above problems, an object of the present invention is to provide an optical coherence tomographic imaging apparatus and tomographic imaging method which, when creating a tomography image of a test object using OCT, especially when the test object is the ocular fundus, can easily image a wide area of the ocular fundus ranging from the retina to the choroid at once.

The present invention provides an optical coherence tomographic imaging apparatus and tomographic imaging method configured as follows.

That is, the present invention provides an optical coherence tomographic imaging apparatus which irradiates a test object with light from a light source, composes interference light using reflected or scattered returning light from the test object, and acquires a tomography image of the test object using the interference light, comprising: low coherence light emitting unit for emitting a first low coherence light and a second low coherence light which differ from each other in center wavelength in order to irradiate the test object with light; first splitting unit for splitting the first low coherence light into a first reference beam and a first measuring beam; second splitting unit for splitting the second low coherence light into a second reference beam and a second measuring beam; first adjustment unit for adjusting focusing position of the first measuring beam; second adjustment unit for adjusting focusing position of the second measuring beam; irradiation unit for irradiating an eye under examination with the first measuring beam adjusted by the first adjustment unit and the second measuring beam adjusted by the second adjustment unit; first detecting unit for detecting an interference light generated from a first returning light and the first reference beam, where the first returning light results from the first measuring beam reflected or scattered by the test object; and second detecting unit for detecting an interference light generated from a second returning light and the second reference beam, where the second returning light results from the second measuring beam reflected or scattered by the test object, characterized in that the focusing position of the first measuring beam adjusted by the first adjustment unit and the focusing position of the second measuring beam adjusted by the second adjustment unit can be adjusted to be at different positions in a depth direction.

Also, the present invention provides an OCT image acquisition method which splits a first low coherence light and a second low coherence light differing from each other in center wavelength into a first reference beam and a first measuring beam and into a second reference beam and a second measuring beam, respectively, to irradiate a test object therewith using irradiation unit, composes interference light using reflected or scattered returning light from the test object, and acquires a tomography image of the test object using the interference light, the OCT image acquisition method comprising: aligning focusing positions of the first measuring beam and the second measuring beam radiated by the irradiation unit with a base layer which serves as a base for the eye under examination; setting the focusing positions of the first measuring beam and the second measuring beam to different depths after the focusing positions of the first measuring beam and the second measuring beam are aligned with the base layer; obtaining a tomographic image of the eye under examination after the focusing positions of the first measuring beam and the second measuring beam are set to different depths.

The present invention can implement an optical coherence tomographic imaging apparatus and tomographic imaging method which, when creating a tomography image of a test object using OCT, especially when the test object is the ocular fundus, can easily make adjustments needed to image a wide area of the ocular fundus ranging from the retina to the choroid at once.

Further features of the present invention will become apparent from the following description of exemplary embodiments with reference to the attached drawings.

BEST MODES FOR CARRYING OUT THE INVENTION

Next, an optical coherence tomographic imaging apparatus and tomographic imaging method according to an exemplary embodiment of the present invention will be described, where the optical coherence tomographic imaging apparatus (OCT apparatus, i.e., an imaging apparatus which uses optical coherence tomography) and tomographic imaging method acquire a tomography image of a test object using OCT.

The OCT apparatus according to the present exemplary embodiment is configured as described in (1) to (6).

On the other hand, the OCT image acquisition method according to the present exemplary embodiment is configured as described in (7) to (11).

(1) The OCT apparatus includes a first interferometer and second interferometer used to obtain interference images from a first low coherence light with a short wavelength and a second low coherence light with a long wavelength, respectively, and first and second flux adjusting units which can adjust luminous fluxes of the first and second low coherence lights, respectively.

To acquire a tomographic image, depth of focus of a first measuring beam derived from the first low coherence light and depth of focus of a second measuring beam derived from the second low coherence light are offset from each other on the same optical axis within a range in which the depth of focus are continuous or overlap.

Consequently, apparent depth of focus is increased, and a wide area of the ocular fundus can be imaged at once.

Also, by using the flux adjusting unit, the focusing position of the first measuring beam can be set to a depth smaller than a layer which provides high reflectivity and the focusing position of the second measuring beam can be set to a depth larger than the layer which provides high reflectivity.

Consequently, an image covering a site deeper than the highly reflective layer which is difficult to measure with the first measuring beam can be obtained with a single imaging scan.

Also, if beam diameters of the first and second measuring beams are adjusted using the flux adjusting unit, an image of a desired resolution can be obtained.

(2) Beam diameters of the first measuring beam and the second measuring beam can be made separately adjustable.

This allows resolution of each measuring beam to be varied.

Also, an imaging range can be extended by adjusting the beam diameters.

These measures allow the resolutions of the first measuring beam and second measuring beam to be adjusted separately, and consequently high-quality OCT images can be obtained over a wide area.

(3) The irradiation unit which irradiates the eye under examination with the first measuring beam and the second measuring beam may be provided with third adjustment unit for adjusting the focusing positions of the first and second measuring beams simultaneously.

This enables simultaneously moving the focusing positions of the first and second measuring beams greatly. Consequently, the time required to adjust the focusing positions can be reduced.

(4) The low coherence light emitting unit for emitting the first and second low coherence lights may include a first light source for generating the first low coherence light and a second light source for generating the second low coherence light.

This enables selecting a desired wavelength according to characteristics of a site to be imaged.

Consequently, high-quality tomographic images can be obtained in a desired area.

(5) The low coherence light emitting unit may include a light source for generating broadband light and a plurality of filters each capable of selecting a single wavelength.

This enables generating the first low coherence light and the second low coherence light using the plurality of filters.

Since a single light source is enough, the apparatus is simplified and variations in oscillations of the first and second low coherence lights are eliminated. Consequently, high-quality tomographic images can be obtained.

(6) The first and second splitting unit may be unified. Alternatively, optical path length adjusting unit for the first reference beam and optical path length adjusting unit for the second reference beam may be unified. This simplifies the apparatus.

(7) The step of creating a tomographic image may include a first step of aligning focusing positions of the first and second measuring beams radiated by the irradiation unit with a layer serving as a base for adjustment, a second step of setting the focusing positions of the first measuring beam and the second measuring beam to different depths after the first step, and a third step of obtaining a tomography image of the eye under examination after the second step. This makes focusing position adjustments easier. Consequently, the tomographic image can be acquired efficiently.

(8) The base layer may be selected from the group consisting of the pigmented epithelial cells layer, nerve fiber layer, and photoreceptor inner and outer segment junction, which are easier to recognize as specific layers in the ocular fundus because of high reflectivity for the first measuring beam.

Consequently this makes it easier to adjust the focusing positions of the first measuring beam and the second measuring beam, allowing a wide area of the ocular fundus to be imaged at high resolution.

(9) Depth of focus of the first measuring beam and depth of focus of the second measuring beam can be made to be continuous or partially overlap in a direction of an optical axis.

Consequently, OCT images can be obtained over a wide area in the direction of the optical axis at once.

(10) Distance between the focusing position of the first measuring beam and the focusing position of the second measuring beam can be set between 20 μm and 1,000 μm.

Consequently, the depth of focus of the first and second measuring beams can be made to be continuous or partially overlap.

If the distance between the focusing positions of the first and second measuring beams is set to 1,000 μm, OCT images can well be obtained over an area ranging from the retina to the choroid at once.

Consequently, OCT images can be obtained over a wide area in the direction of the optical axis at once.

(11) The focusing position of the first measuring beam which is the low coherence light with a short wavelength can be set to a depth smaller than the base layer and the focusing position of the second measuring beam which is the low coherence light with a long wavelength can be set to a depth larger than the base layer.

This allows the second measuring beam to reach a site which has high reflectivity for the first measuring beam and is located deeper than a layer relatively opaque to the first measuring beam. Consequently, a wide area of the ocular fundus can be imaged.

As another exemplary embodiment, a program which causes a computer to execute the optical coherence tomographic imaging method according to the above-described exemplary embodiment described above may be stored in a computer-readable storage medium (examples of which include a flexible disk, hard disk, optical disk, magneto-optical disk, CD-ROM, CD-R, magnetic tape, non-volatile memory card, ROM, EEPROM, and Blue-ray disk). Besides, the program which causes a computer to execute the optical coherence tomographic imaging method described above can also be an exemplary embodiment.

Next, embodiments of the present invention will be described.

[First Embodiment]

In a first embodiment, an OCT apparatus resulting from application of the present invention will be described.

An apparatus which acquires tomographic images (OCT images) of a test object, which in this case is an eye under examination, will be described here.

The OCT apparatus described here is a Fourier Domain OCT apparatus. First and second low coherence light sources are used.

Figure 1:
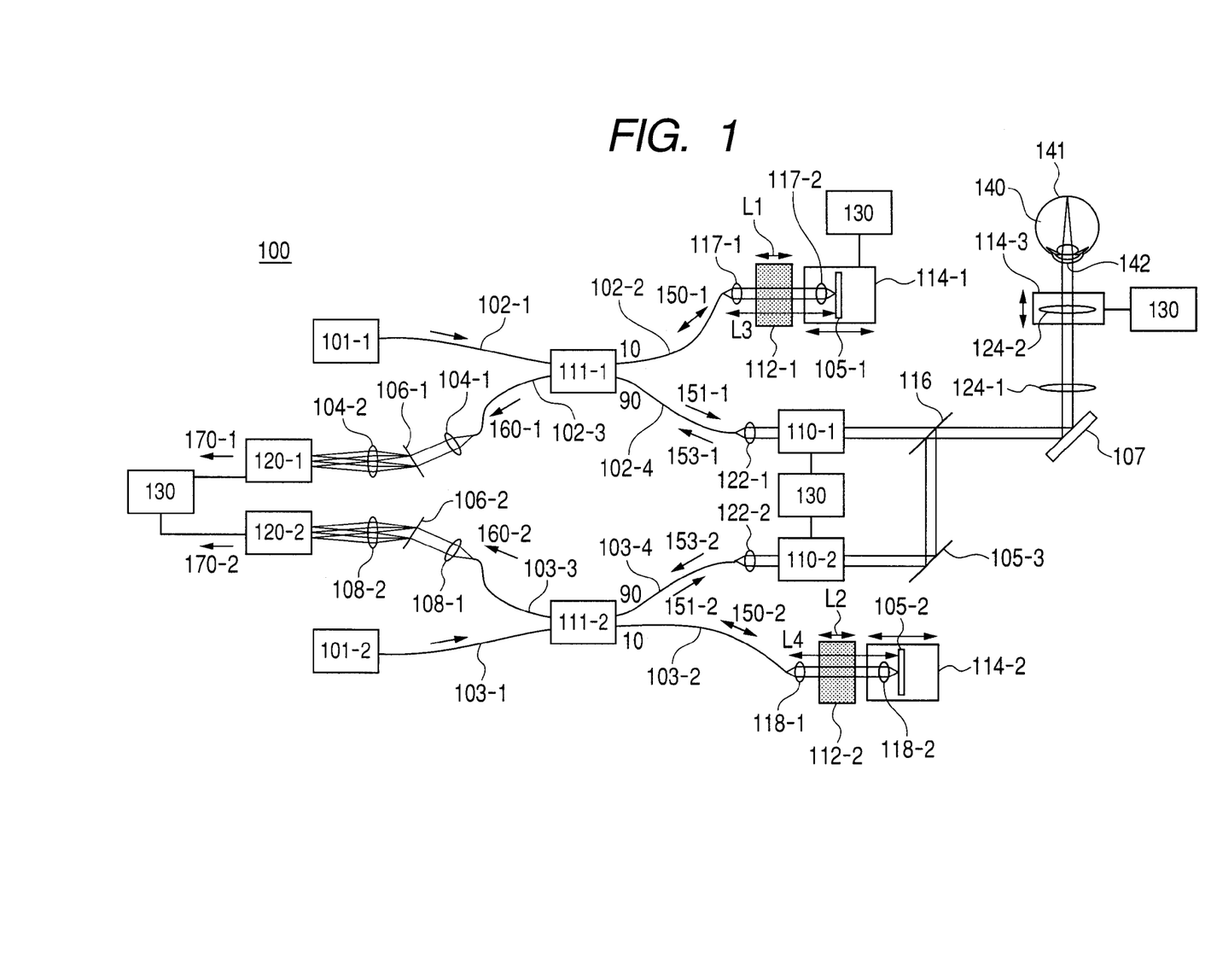
FIG. 1 is a diagram for illustrating a configuration of an optical system of an OCT apparatus according to a first embodiment of the present invention.

First, an overall configuration of an optical system of the OCT apparatus according to the present embodiment will be outlined with reference to FIG. 1.

Incidentally, a controlling and signal processing unit 130 is shown at multiple locations in FIG. 1 for the sake of illustration, but actually is the same one.

As illustrated in FIG. 1, the OCT apparatus 100 according to the present embodiment includes two Michelson interferometers as a whole, and measuring beams enter the eye under examination along the same optical axis by being combined by a dichroic mirror 116. Light sources 101-1 and 101-2 are low coherence light sources which differ from each other in center wavelength. The light source 101-1 emits a first low coherence light and the light source 101-2 emits a second low coherence light.

The light emitted from the light source 101-1 is passed through an optical fiber 102-1 and split into a reference beam 150-1 (first reference beam) and measuring beam 151-1 (first measuring beam) at an intensity ratio of 10:90 by a fiber coupler 111-1 (first splitting unit).

The measuring beam 151-1 is transmitted through the dichroic mirror 116 and enters a test object, i.e., an eye under examination 140. Then, the measuring beam 151-1 is returned as a returning light 153-1 (first returning light) by being reflected or scattered by the eye under examination 140.

The returning light 153-1 is transmitted through the dichroic mirror 116 again, and then combined with the reference beam 150-1 by the fiber coupler 111-1.

The reference beam 150-1 and returning light 153-1 are combined into an interference light, which is then separated into spectral components at different wavelengths by a transmission grating 106-1. Then, the interference light enters a line camera 120-1 (first detecting unit).

The line camera 120-1 converts light intensity at each site (wavelength) into a voltage and sends a resulting signal 170-1 to the controlling and signal processing unit 130.

On the other hand, the light emitted from the light source 101-2 is similarly passed through an optical fiber 103-1 and split into a reference beam 150-2 (second reference beam) and measuring beam 151-2 (second measuring beam) at an intensity ratio of 10:90 by a fiber coupler 111-2 (second splitting unit).

The measuring beam 151-2 is reflected by the dichroic mirror 116 and enters the eye under examination 140. Then, the measuring beam 151-2 is returned as a returning light 153-2 (second returning light) by being reflected or scattered by the eye under examination 140.

The returning light 153-2 is reflected by the dichroic mirror 116 again, and then combined with the reference beam 150-2 by the fiber coupler 111-2.

The reference beam 150-2 and returning light 153-2 are combined into an interference light, which is then separated into spectral components at different wavelengths by a transmission grating 106-2. Then, the interference light enters a line camera 120-2 (second detecting unit).

The line camera 120-2 converts light intensity at each site into a voltage and sends a resulting signal 170-2 to the controlling and signal processing unit 130.

The controlling and signal processing unit 130 processes the signal 170-1 and signal 170-2 and thereby constructs a tomography image of the eye under examination 140.

Although according to the present embodiment, the first low coherence light source and second low coherence light source respectively generate the first low coherence light and second low coherence light which differ from each other in center wavelength, the present invention is not limited to this, and the present invention may be configured to generate the first low coherence light and second low coherence light which differ from each other in center wavelength using a single light source if the configuration includes a light source such as an SC (Supercontinuum) light source (with an oscillation wavelength of 700 nm to 2,000 nm) for generating broadband light and a plurality of filters each capable of selecting a single wavelength.

Next, a configuration related to the light source 101-1 will be described, where the light source 101-1 is the first low coherence light source.

The light source 101-1 is an SLD (Super Luminescent Diode) which is a typical low coherence light source.

Center wavelength of the light source 101-1 is 830 nm and bandwidth is 50 nm.

The bandwidth is an important parameter, which affects resolution in the optical axis direction of a resulting tomography image.

Also, although an SLD has been selected here, another type of light source such as an ASE (Amplified Spontaneous Emission) light source may be used alternatively, provided the light source can emit low coherence light.

Next, the optical path of the reference beam 150-1 will be described.

The reference beam 150-1 resulting from the split done by the fiber coupler 111-1 is led to a lens 117-1 through an optical fiber 102-2 and adjusted to be a parallel light. Next, the reference beam 150-1 is collected by a lens 117-2, reflected by a mirror 105-1, and thereby led to the fiber coupler 111-1 again.

The reference beam 150-1 is passed through dispersion compensating glass 112-1 intended to compensate the reference beam 150-1 for dispersion caused when the measuring beam 151-1 travels to and from the eye under examination 140. Thickness L1 of the dispersion compensating glass 112-1 is determined based on relationship between the wavelength and the arrangement of the eye under examination 140, a flux adjusting unit 110-1, and lenses 124-1 and 124-2.

Optical path length L3 is adjusted to make optical distance from the fiber coupler 111-1 to the eye under examination equal to optical distance from the fiber coupler 111-1 to the mirror 105-1.

Furthermore, the mirror 105-1 is fixed to a motor-driven stage 114-1, allowing the optical path length of the reference beam 150-1 to be adjusted and controlled by moving the motor-driven stage 114-1 in the directions indicated by an arrow.

Also, the motor-driven stage 114-1 can be controlled at high speed by the controlling and signal processing unit 130.

Next, an optical path of the reference beam 150-2 will be described.

The reference beam 150-2 resulting from the split done by the fiber coupler 111-2 is led to a lens 118-1 through an optical fiber 103-2 and adjusted to be a parallel light. Next, the reference beam 150-2 is collected by a lens 118-2, reflected by a mirror 105-2, and thereby led to the fiber coupler 111-2 again.

The reference beam 150-2 is passed through dispersion compensating glass 112-2 intended to compensate the reference beam 150-2 for dispersion caused when the measuring beam 151-2 travels to and from the eye under examination 140. Thickness L2 of the dispersion compensating glass 112-2 is determined based on relationship between the wavelength and the arrangement of the eye under examination 140, a flux adjusting unit 110-2, and the lenses 124-1 and 124-2.

Optical path length L4 is adjusted to make optical distance from the fiber coupler 111-2 to the eye under examination equal to optical distance from the fiber coupler 111-2 to the mirror 105-2.

Furthermore, the mirror 105-2 is fixed to a motor-driven stage 114-2, allowing the optical path length of the reference beam 150-2 to be adjusted and controlled by moving the motor-driven stage 114-2 in the directions indicated by an arrow.

Also, the motor-driven stage 114-2 can be controlled at high speed by the controlling and signal processing unit 130.

Next, an optical path of the measuring beam 151-1 will be described.

The measuring beam 151-1 resulting from the split done by the fiber coupler 111-1 is converted into a parallel light 2.5 mm in beam diameter by a lens 122-1 and led to the flux adjusting unit 110-1.

The flux adjusting unit 110-1 can adjust beam diameter and the degree of convergence based on a signal from the controlling and signal processing unit 130.

The beam diameter of the measuring beam 151-1 only needs to be smaller than the diameter of the pupil, and is adjustable here in the range of 1 mm to 6 mm.

On the other hand, the degree of convergence is adjusted to vary the focusing position of the measuring beam 151-1 on the ocular fundus of the eye under examination 140, allowing to vary the focusing position on the ocular fundus by 1 mm in this case.

The focusing position only needs to be adjustable at least by an amount equal to the thickness of the retina, and the amount may be determined according to a range of observations.

After passing through the flux adjusting unit 110-1, the measuring beam 151-1 is led to the dichroic mirror 116. The dichroic mirror 116 has the characteristics of transmitting the measuring beam 151-1 and returning light 153-1 of the light source 101-1 and reflecting the measuring beam 151-2 and returning light 153-2 of the light source 101-2.

After being transmitted through the dichroic mirror 116, the measuring beam 151-1 enters an X-Y scanner 107.

Although illustrated as being a single mirror for the sake of simplicity, actually the X-Y scanner 107 includes two mirrors, i.e., X-scanning mirror and Y-scanning mirror, placed close to each other so that the retina 141 can be raster scanned in a direction perpendicular to the optical axis.

The center of the measuring beam 151-1 has been adjusted to coincide with the center of rotation of the mirrors of the X-Y scanner 107.

The lenses 124-1 and 124-2 make up an optical system which scans the retina 141 with the measuring beam 151-1 with a fulcrum placed near the cornea 142.

Focal lengths of the lenses 124-1 and 124-2 are 50 mm and 40 mm, respectively.

A motor-driven stage 114-3 can move in the directions indicated by an arrow, allowing position of the accompanying lens 124-2 to be adjusted and controlled. As the position of the lens 124-2 is adjusted by the controlling and signal processing unit 130, the measuring beam 151-1 can be collected and focused on the retina 141 of the eye under examination 140, enabling observations.

This configuration also accommodates situations where the eye under examination 140 is ametropic.

After entering the eye under examination 140, the measuring beam 151-1 becomes the returning light 153-1 due to reflection and scattering from the retina 141 and travels backward along the optical path of the measuring beam 151-1.

The returning light 153-1 is transmitted through the dichroic mirror 116 and led to the line camera 120-1 through the fiber coupler 111-1.

Next, a configuration related to the light source 101-2 will be described, where the light source 101-2 is the second low coherence light source.

The light source 101-2 is an SLD as in the case of the light source 101-1, and has a wavelength of 1,050 nm and a bandwidth of 50 nm.

The wavelength of the light source 101-2 only needs to be such that will not cause interference with the measuring beam 151-1 of the light source 101-1.

Next, an optical path of the measuring beam 151-2 will be described.

After passing through the flux adjusting unit 110-2, the measuring beam 151-2 is reflected by a mirror 105-3 and led to the dichroic mirror 116.

The measuring beam 151-2 from the light source 101-2 is reflected by the dichroic mirror 116. Then, the measuring beam 151-2 is combined with the measuring beam 151-1, and the resulting light travels along the same optical axis as the measuring beam 151-1.

The light reflected or scattered by the retina 141 travels as the returning light 153-2 along an optical path opposite in direction to the measuring beam 151-2.

The returning light 153-2 is reflected by the dichroic mirror 116 and separated from the returning light 153-1.

The rest of the optical path of the measuring beam 151-2 is approximately the same as the optical path of the measuring beam 151-1, and thus description thereof will be omitted.

Next, a configuration of a measurement system on the OCT apparatus according to the present embodiment will be described.

The OCT apparatus 100 includes two Michelson interferometers put together, and can obtain a tomography image (OCT image) represented by intensities of interference signals from the interferometers. Now, a measurement system of the interferometer will be described, where the measurement system uses the measuring beam 151-1 emitted from the light source 101-1.

The returning light 153-1 which is the light reflected or scattered by the retina 141 is combined with the reference beam 150-1 by the fiber coupler 111-1.

The combined light 160-1 is separated into spectral components at different wavelengths by the transmission grating 106-1, and the spectral components are collected by a lens 104-2. Then, light intensity at each site (wavelength) is converted into a voltage by the line camera 120-1.

Specifically, interference fringes are observed in a spectral region on a wavelength scale of the line camera 120-1.

A group of resulting electrical signals is subjected to data processing by the controlling and signal processing unit 130 to form a tomography image.

The line camera has 1,024 pixels and can obtain intensities at 1,024 different wavelengths of the combined light 160-1.

An interferometer's measurement system which uses the measuring beam 151-2 emitted from the light source 101-2 is approximately the same as the interferometer's measurement system which uses the measuring beam 151-1 emitted from the light source 101-1, and thus description thereof will be omitted.

Next, a focusing position adjustment method which is a feature of the present invention will be described concretely with reference to FIG. 2, FIGS. 3A to 3C, and FIG. 4.

Figure 2:
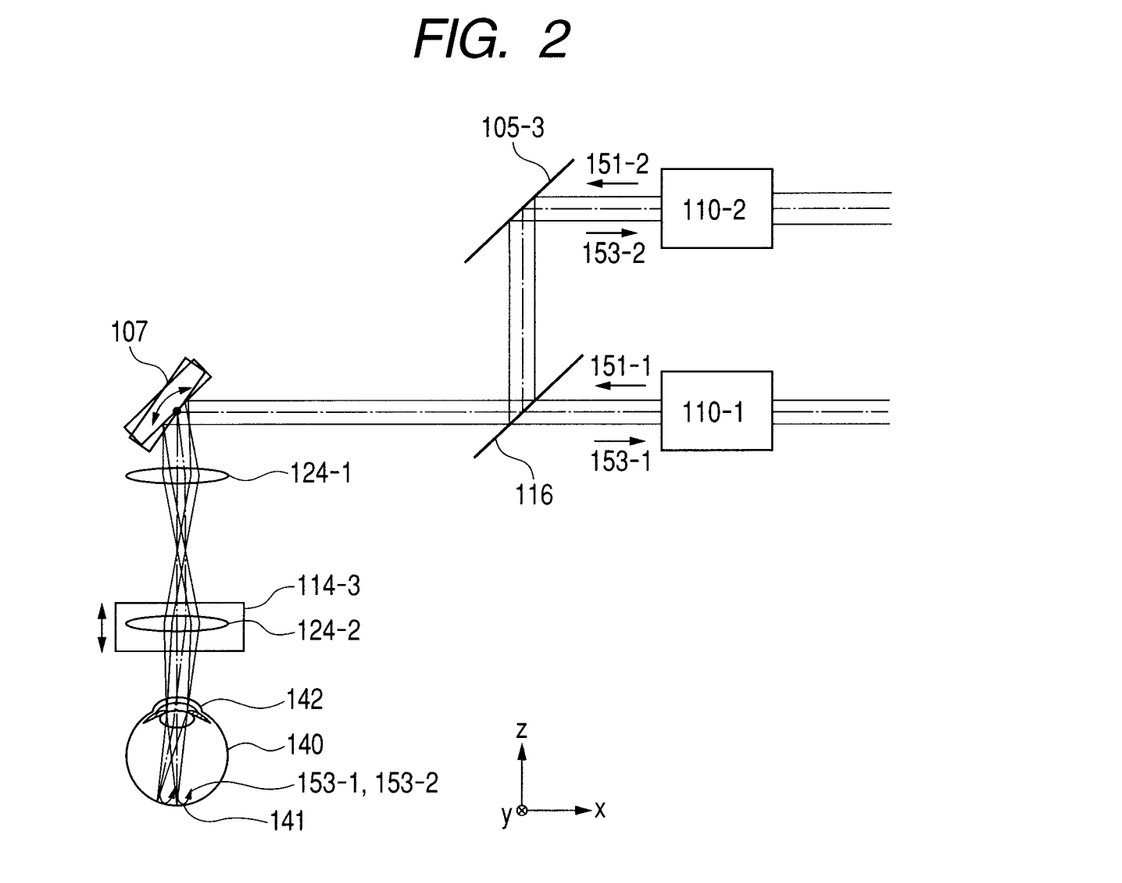
FIG. 2 is a diagram for illustrating a configuration of the optical system of the OCT apparatus according to the first embodiment of the present invention.

FIG. 2 is a diagram for illustrating the focusing position adjustment method. That is, FIG. 2 shows that part of the optical system which causes the measuring beams to enter the eye under examination, where the same components as those in FIG. 1 are denoted by the same reference numerals as the corresponding components in FIG. 1.

Generally, when the retina in the ocular fundus is observed, the retina is scanned with measuring beam for safety reasons. Also, in the present embodiment, measurements are actually taken by scanning the retina with measuring beam.

Figure 3A:
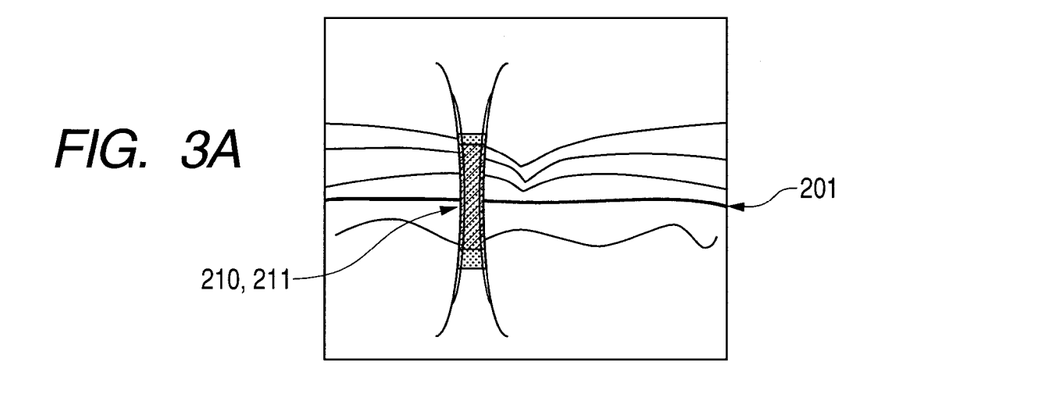
FIGS. 3A, 3B, and 3C are diagrams for illustrating a focusing position adjustment method for the OCT apparatus according to the first embodiment of the present invention.
Figure 3B:
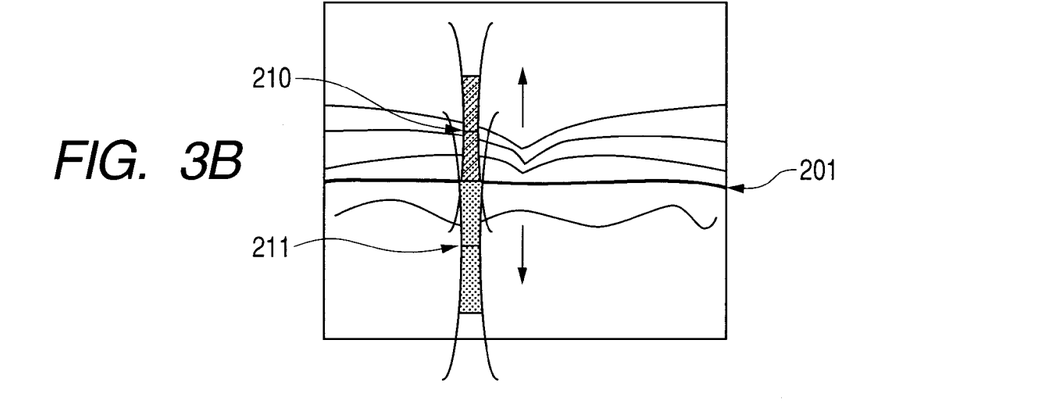
Figure 3C:
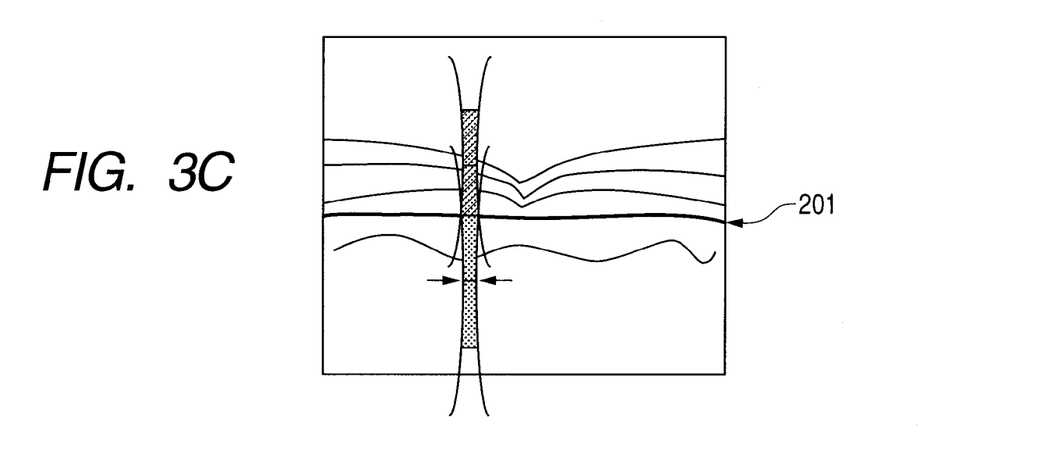

In FIGS. 3A to 3C, a layer 201 (pigmented epithelial cells layer: RPE layer) has a high reflectivity for a light source with a short wavelength, where the focusing position of the measuring beam 151-1 is denoted by 210 and focusing position of the measuring beam 151-2 is denoted by 211.

In the adjustment method according to the present embodiment, steps below may be carried out, for example, successively in sequence or by returning to previous steps as required.

Alternatively, the following steps may be carried out automatically using a computer.

To begin with, in a first step, one layer in the retina is brought into focus using the lens 124-2 and flux adjusting units 110-1 and 110-2.

The layer brought into focus is not limited as long as the layer is selected from the layers of the retina, but desirably a highly reflective layer, which is easy to bring into focus, is used as the base layer which is to be brought into focus.

Figure 4:
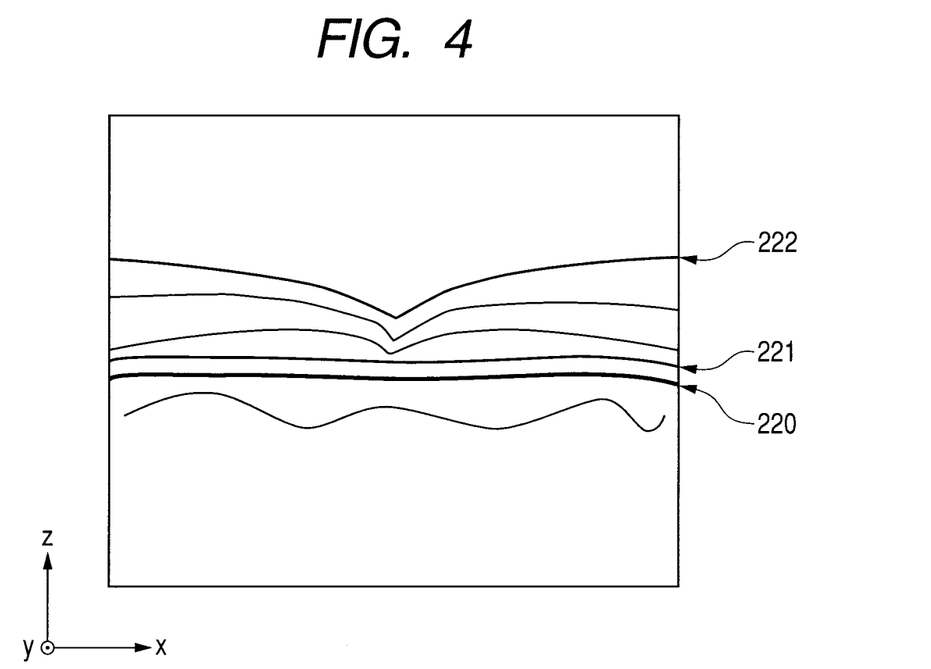
FIG. 4 is a diagram for illustrating the focusing position adjustment method for the OCT apparatus according to the first embodiment of the present invention.

Highly reflective layers on the retina include, for example, the pigmented epithelial cells layer 220, photoreceptor inner and outer segment junction 221, and nerve fiber layer 222 (FIG. 4).

In this case, the pigmented epithelial cells layer (RPE layer) which has a high reflectivity for the wavelength of the light source 101-1 is brought into focus (FIG. 3A).

Adjustments are made by the lens 124-2 and the flux adjusting units 110-1 and 110-2 under the control of the controlling and signal processing unit 130 (FIG. 2).

Specifically, the returning lights 153-1 and 153-2 from the retina 141 are detected by the line cameras 120-1 and 120-2 and adjustments are made so as to approximately maximize the intensities of the returning lights 153-1 and 153-2.

Next, in a second step, the focusing positions 210 and 211 are moved using the flux adjusting unit 110-1 (first adjustment unit) and flux adjusting unit 110-2 (second adjustment unit).

The focusing positions are moved by the flux adjusting units by varying the degree of beam convergence under the control of the controlling and signal processing unit 130.

When the flux adjusting units adjust the degree of flux convergence and thereby cause a light slightly more converged than a parallel beam to enter the X-Y scanner 107, the focusing positions move toward the cornea, i.e., in the Z direction (depth direction) of the XYZ coordinate system from the focusing positions established in the first step.

Conversely, when the flux adjusting units cause a light slightly more diverged than a parallel beam to enter the X-Y scanner 107, the focusing positions move away from the cornea.

Consequently, the focusing position is moved toward the cornea in the case of the short-wavelength measuring beam 151-1 of the light source 101-1 not easily transmitted through the RPE layer and the focusing position is moved away from the cornea in the case of the long-wavelength measuring beam 151-2 of the light source 101-2 transmitted through the RPE layer.

Regarding the amounts of focusing position movement, each focusing position is moved to the extent that the RPE layer will be kept within the depth of focus of a single measuring beam.

Also, adjustments are made to the extent that the depth of focus will be continuous or partially overlap.

Generally, the depth of focus is expressed as follows (Expression 1).

$$\text{Focus depth} = 2Z_R = 2\pi\omega_o^2/\lambda \quad \text{(Expression 1)}$$

wherein $\lambda$ is center wavelength of low coherence light source and $\omega_o$ is spot radius of low coherence light.

The focusing positions of incident measuring beams with a beam diameter of 1 mm are adjusted to be 500 μm away from the RPE layer in opposite directions by the flux adjusting units 110-1 and 110-2 (FIG. 3B). Consequently, focusing position distance between the measuring beams 151-1 and 151-2 is 1,000 μm.

Next, the flux adjusting unit 110-2 adjusts the measuring beam 151-2 so that focus spot sizes of the measuring beams 151-1 and 151-2 will be equal to each other.

A light longer in wavelength has a larger depth of focus and spot size than a light shorter in wavelength, resulting in a larger spot size, and the beam diameter of the measuring beam 151-2 is changed here to equalize resolutions in the direction perpendicular to the optical axis.

In this case, the beam diameter of the measuring beam 151-2 is adjusted to be 1.01 mm (FIG. 3C).

Next, in a third step, the mirrors 105-1 and 105-2 are adjusted using the motor-driven stages 114-1 and 114-2.

Consequently, the optical path lengths of the reference beams 150-1 and 150-2 are adjusted, causing interference between the reference beam 150-1 and returning light 153-1 as well as between the reference beam 150-2 and returning light 153-2.

Next, a method for obtaining a tomography image using the OCT apparatus will be described.

The OCT apparatus 100 can obtain interference fringes using the line cameras 120-1 and 120-2 by controlling the X-Y scanner 107, and thereby obtain tomography images of the retina 141 (FIG. 1).

Now, a method for obtaining a tomography image (on a plane parallel to the optical axis) of the retina 141 will be described with reference to FIGS. 5A to 5C.

Figure 5A:
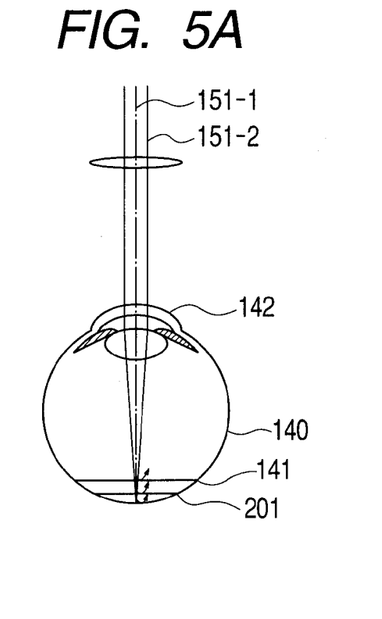
FIGS. 5A, 5B, and 5C are diagrams for illustrating an imaging method for the OCT apparatus according to the first embodiment of the present invention.

FIG. 5A is a schematic diagram of the eye under examination 140, illustrating how the eye under examination 140 is observed using the OCT apparatus 100.

As illustrated in FIG. 5A, upon entering the retina 141 through the cornea 142, the measuring beams 151-1 and 151-2 become the returning lights 153-1 and 153-2 after going through reflections and scattering at various locations.

Then, the returning lights 153-1 and 153-2 reach the line cameras 120-1 and 120-2 with time delays caused at the various locations.

In this case, since the light sources 101-1 and 101-2 have wide bandwidths and short spatial coherence lengths, when reference beam paths and measuring beam paths are approximately equal in optical path length, the line cameras 120-1 and 120-2 can detect interference fringes.

As described above, the line cameras 120-1 and 120-2 provide interference fringes in a spectral region on a wavelength scale.

Next, the interference fringes, i.e., information on the wavelength scale, are converted into interference fringes on an optical frequency scale by taking characteristics of the line cameras 120-1 and 120-2 and transmission gratings 106-1 and 106-2 into consideration.

Furthermore, the inverse Fourier transform of the resulting interference fringes on the optical frequency scale is computed to obtain depth direction information.

Figure 5B:
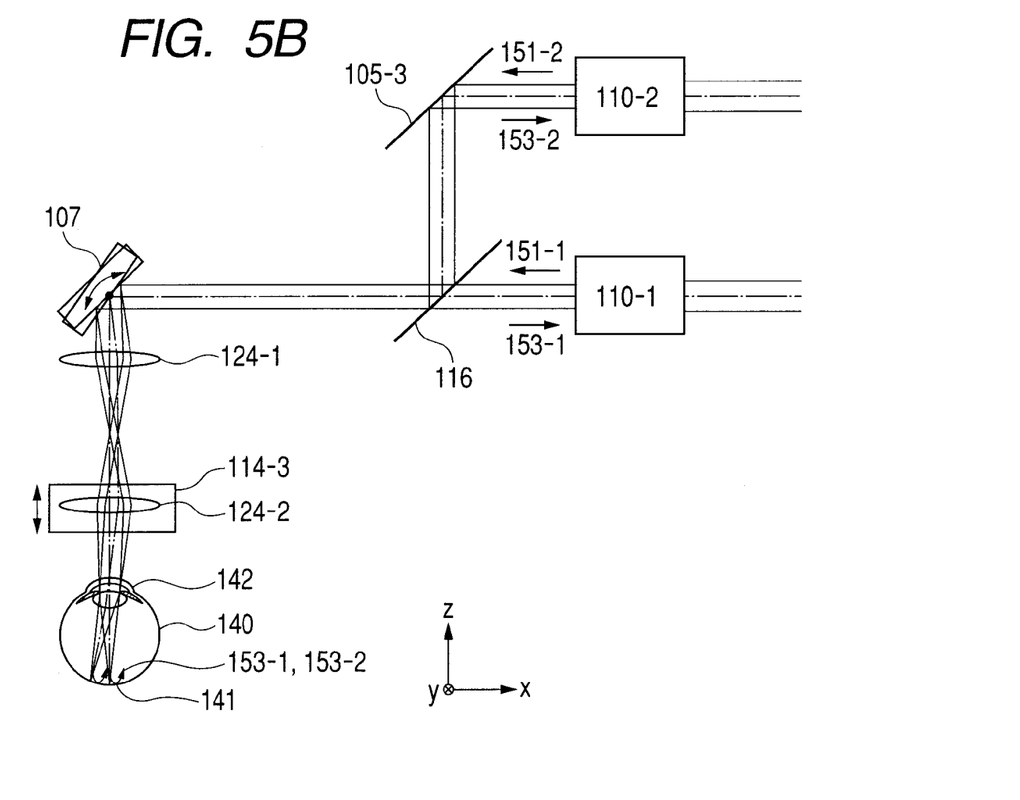
Figure 5C:
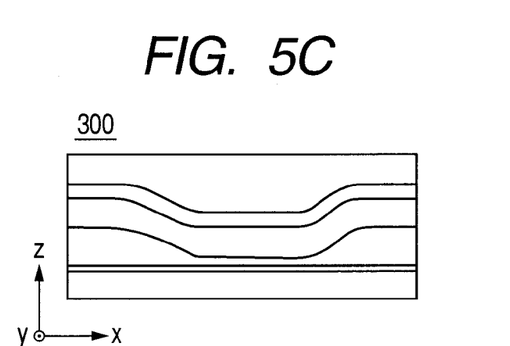

Then, as illustrated in FIG. 5B, if interference fringes are detected by driving the X axis of the X-Y scanner 107, an interference fringe, i.e., depth direction information, can be obtained for each X-axis position.

This provides two-dimensional intensity distributions of returning lights 153-1 and 153-2 on an X-Z plane. Then, based on position information from the flux adjusting units 110-1 and 110-2 and the lens 124-2, the controlling and signal processing unit 130 superimposes the two-dimensional intensity distributions to obtain a tomography image 300 (FIG. 5C).

Originally, the tomography image 300 is made up of intensities of returning lights 153 arranged in an array as described above, where the intensities are displayed, for example, by being put into a gray scale. In FIG. 5C, only boundaries of the obtained tomography image are highlighted.

Figure 6:
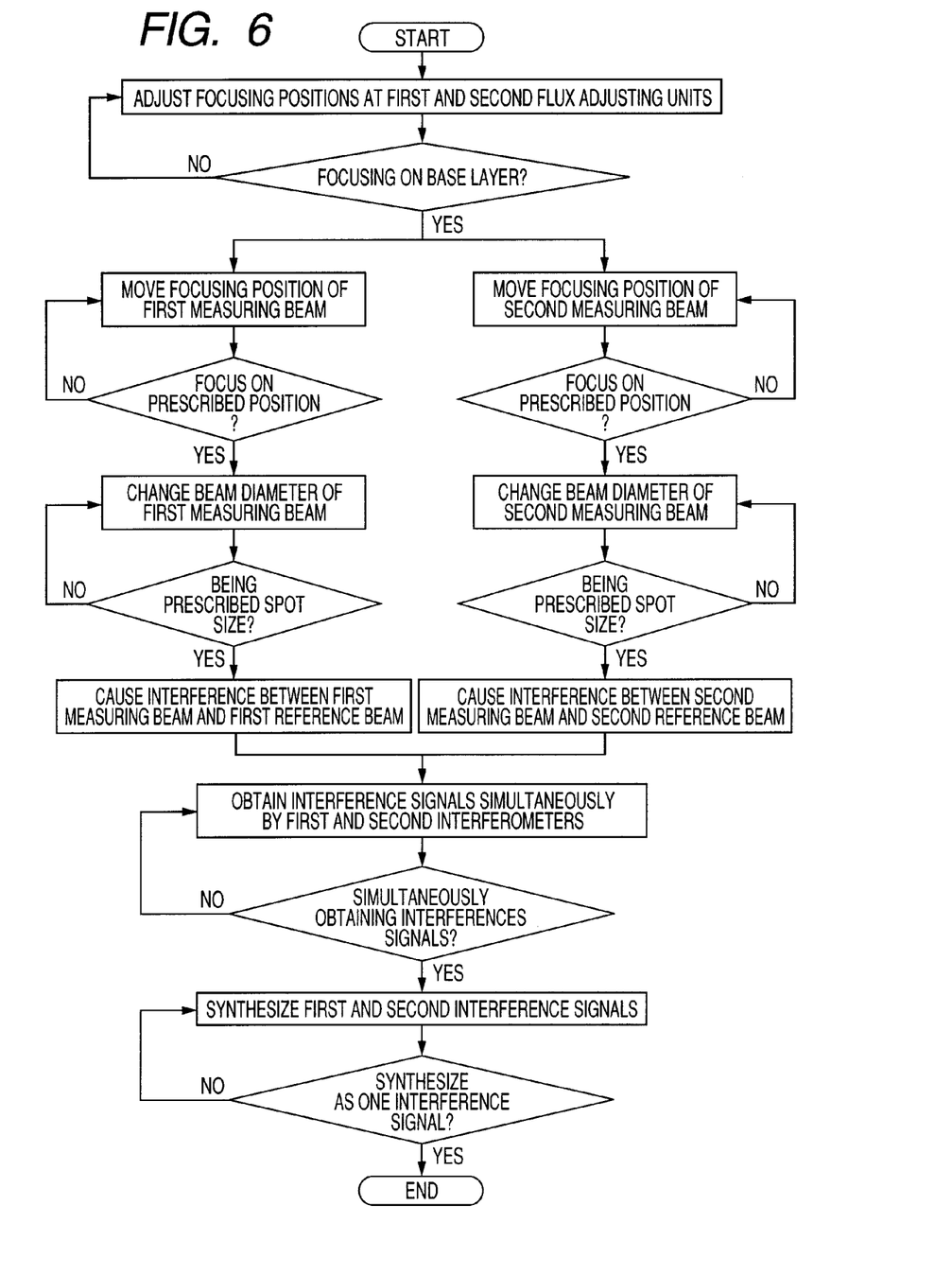
FIG. 6 is a flowchart for illustrating the imaging method for the OCT apparatus according to the first embodiment of the present invention.

FIG. 6 is a flowchart showing the steps described above.

As described above, by creating a tomography image of the ocular fundus, an OCT image of a wide area on both sides of the RPE layer can be obtained at once. Also, adjustments can be made easily and measurement time can be reduced in creating a tomographic image of a wide area using measuring beams of different wavelengths.

Incidentally, although in the present embodiment, the focusing positions of the measuring beams 151-1 and 151-2 are varied on the same optical axis, even when the focusing positions are not on the same optical axis, the present method is applicable if an interference image can be composed from position information.

[Second Embodiment]

A configuration of an optical system of an OCT apparatus according to a second embodiment will be described with reference to FIG. 7, where the configuration is similar to that of the first embodiment except that a mirror for optical path length adjustment is shared between reference beams.

Figure 7:
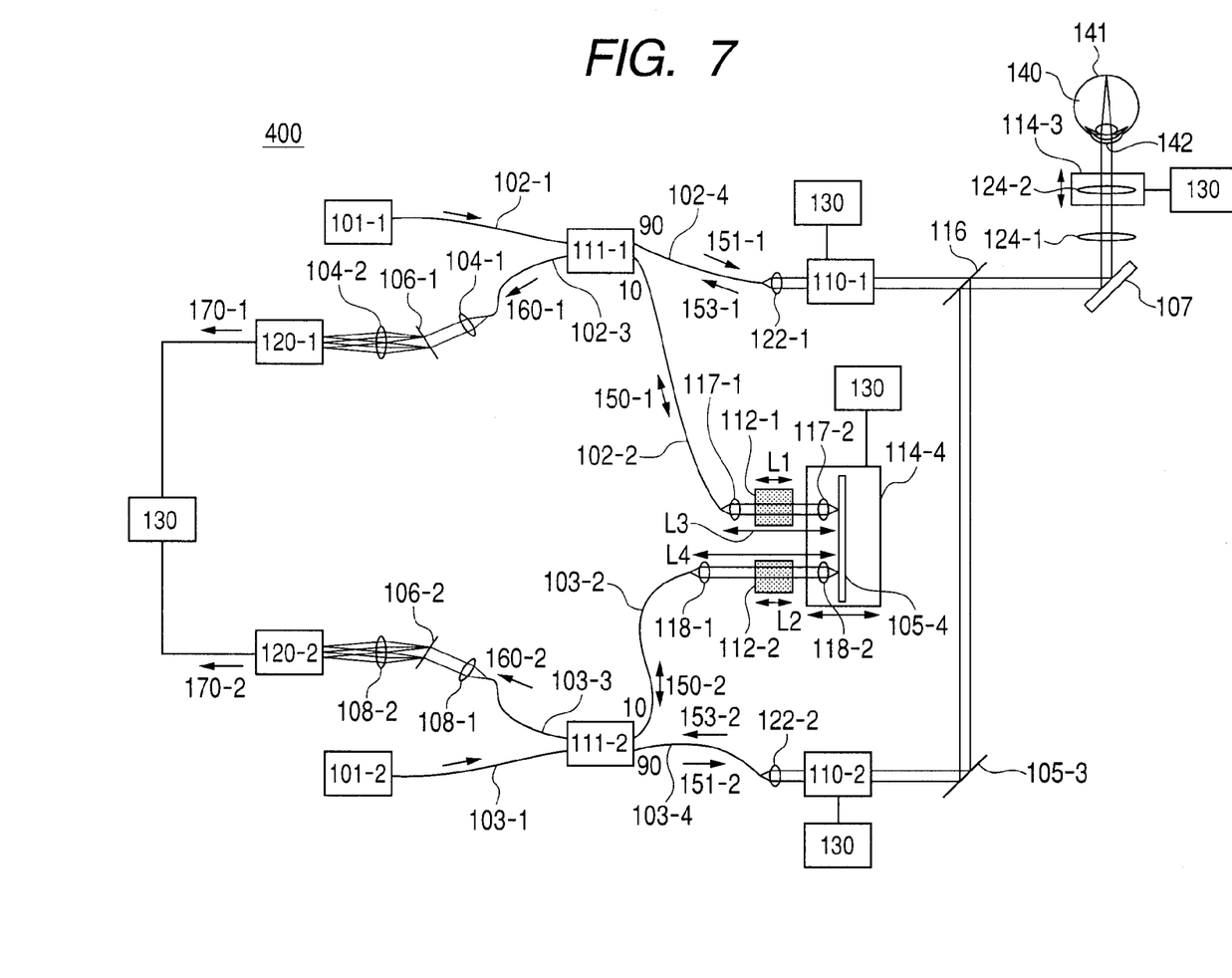
FIG. 7 is a diagram for illustrating a configuration of an optical system of an OCT apparatus according to a second embodiment of the present invention.

In FIG. 7, the same components as those in FIG. 1 are denoted by the same reference numerals as the corresponding components in FIG. 1, and redundant description thereof will be omitted.

In FIG. 7, the OCT apparatus 400 includes a mirror 105-4 and motor-driven stage 114-4.

The present embodiment simplifies the OCT apparatus 400 by using a single mirror and a single motor-driven stage instead of the mirrors 105-1 and 105-2 and the motor-driven stages 114-1 and 114-2 in FIG. 1.

Except for the use of the single mirror and single motor-driven stage, the present embodiment has much the same basic configuration as the first embodiment.

Next, the configuration of the optical system of the OCT apparatus according to the present embodiment will be described.

As illustrated in FIG. 7, the OCT apparatus 400 according to the present embodiment includes two Michelson interferometers as a whole, and measuring beams enter the eye under examination along the same optical axis by being combined by the dichroic mirror 116. In FIG. 7, after entering the object to be observed, i.e., the eye under examination 140, the measuring beam 151-1 goes through reflections and scattering on the retina 141 and returns as the returning light 153-1. Then, the returning light 153-1 of the measuring beam 151-1 is combined with the reference beam 150-1 by the fiber coupler 111-1.

The combined reference beam 150-1 and returning light 153-1 are spectrally separated by the transmission grating 106-1 and detected by the line camera 120-1.

The measuring beam 151-2 goes through approximately the same process, and thus description thereof will be omitted.

Next, the reference beams 150-1 and 150-2 will be described.

The reference beam 150-1 resulting from the split done by the fiber coupler 111-1 is led to the lens 117-1 through the optical fiber 102-2 and adjusted to be a parallel light.

Next, the reference beam 150-1 is collected by the lens 117-2, reflected by a mirror 105-4, and thereby led to the fiber coupler 111-1 again.

Here, the reference beam 150-1 is passed through the dispersion compensating glass 112-1 intended to compensate the reference beam 150-1 for dispersion caused when the measuring beam 151-1 travels to and from the eye under examination 140.

The thickness L1 of the dispersion compensating glass 112-1 is determined based on relationship between the wavelength and the arrangement of the eye under examination 140, flux adjusting unit 110-1, and lenses 124-1 and 124-2. The optical path length L3 is adjusted to make optical distance from the fiber coupler 111-1 to the eye under examination equal to optical distance from the fiber coupler 111-1 to the mirror 105-4.

Similarly, the reference beam 150-2 resulting from the split done by the fiber coupler 111-2 is led to the lens 118-1 through the optical fiber 103-2 and adjusted to be a parallel light.

Next, the reference beam 150-2 is collected by the lens 118-2, reflected by a mirror 105-4, and thereby led to the fiber coupler 111-2 again.

The reference beam 150-2 is passed through the dispersion compensating glass 112-2 intended to compensate the reference beam 150-2 for dispersion caused when the measuring beam 151-2 travels to and from the eye under examination 140. The thickness L2 of the dispersion compensating glass 112-2 is determined based on relationship between the wavelength and the arrangement of the eye under examination 140, flux adjusting unit 110-2, and lenses 124-1 and 124-2.

The optical path length L4 is adjusted to make the optical distance from the fiber coupler 111-2 to the eye under examination equal to optical distance from the fiber coupler 111-2 to the mirror 105-4.

Furthermore, the mirror 105-4 is fixed to the motor-driven stage 114-4, allowing the optical path lengths of the reference beams 150-1 and 150-2 to be adjusted and controlled by moving the motor-driven stage 114-4 in the directions indicated by an arrow.

Also, the motor-driven stage 114-4 can be controlled at high speed by the controlling and signal processing unit 130. Consequently, optical path lengths of the reference beams 150-1 and 150-2 can be controlled simultaneously by the single mirror 105-4 and single motor-driven stage 114-4.

The rest of the configuration of the optical system as well as a measuring method are the same as the first embodiment, and thus description thereof will be omitted.

As described above, by unifying adjustments of the reference beam paths, the second embodiment provides the advantage of being able to simplify the equipment configuration and downsize the apparatus in addition to the advantages of the first embodiment.

[Other Embodiments]

Aspects of the present invention can also be realized by a computer of a system or apparatus (or devices such as a CPU or MPU) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (e.g., computer-readable medium).

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2009-123920, filed May 22, 2009, which is hereby incorporated by reference herein in its entirety.

The invention claimed is:

1. An imaging apparatus that irradiates an object with a first measuring beam and a second measuring beam that differ from each other in a center wavelength, and acquires an image of the object using returning light from the object, the imaging apparatus comprising:
    a first adjustment unit for adjusting a focusing position of the first measuring beam in a depth direction;
    a second adjustment unit for adjusting a focusing position of the second measuring beam in the depth direction; and
    a controlling unit for controlling, after the focusing position of the first measuring beam and the focusing position of the second measuring beam are adjusted based on returning light from the object, at least one of the first adjustment unit and the second adjustment unit such that the focusing position of the first measuring beam and the focusing position of the second measuring beam are at different positions in the depth direction.

2. The imaging apparatus according to claim 1, wherein the first adjustment unit and the second adjustment unit can adjust a beam diameter of the first measuring beam and a beam diameter of the second measuring beam, respectively.

3. The imaging apparatus according to claim 1, further comprising a third adjustment unit for adjusting the adjusted focusing positions of the first measuring beam and the second measuring beam, simultaneously,
    wherein the first adjustment unit, the second adjustment unit, and the third adjustment unit adjust the focusing positions of the first measuring beam and the second measuring beam.

4. The imaging apparatus according to claim 1, further comprising a light emitting unit for emitting a first light beam and a second light beam that differ from each other in a center wavelength in order to irradiate the object with light,
    wherein the light emitting unit includes a first light source for generating the first light beam and a second light source for generating the second light beam.

5. The imaging apparatus according to claim 1, further comprising a light emitting unit for emitting a first light beam and a second light beam that differ from each other in a center wavelength in order to irradiate the object with light, wherein the light emitting unit includes a light source for generating broadband light and a plurality of filters each capable of selecting a single wavelength, and wherein the plurality of filters is used to generate the first light beam and the second light beam.

6. The imaging apparatus according to claim 1, further comprising a light emitting unit for emitting a first light beam and a second light beam that differ from each other in a center wavelength in order to irradiate the object with light;

a first splitting unit for splitting the first light beam into a first reference beam and the first measuring beam; and a second splitting unit for splitting the second light beam into a second reference beam and the second measuring beam, wherein an optical path length adjusting unit for the first reference beam and an optical path length adjusting unit for the second reference beam are common.

7. An imaging method that acquires an image of an object using a returning light beam from the object by irradiating, with an irradiation unit, the object with a first measuring beam and a second measuring beam that differ from each other in a center wavelength, the imaging method comprising:

after a focusing position of the first measuring beam and a focusing position of the second measuring beam are adjusted based on returning light from the object, controlling at least one of a first adjustment unit for adjusting the focusing position of the first measuring beam in a depth direction and a second adjustment unit for adjusting the focusing position of the second measuring beam in the depth direction, such that the focusing position of the first measuring beam and the focusing position of the second measuring beam are at different positions in the depth direction.

8. The imaging method according to claim 7, wherein a depth of focus of the first measuring beam and a depth of focus of the second measuring beam are continuous or partially overlap in a direction of an optical axis.

9. The imaging method according to claim 7, wherein a distance between the focusing position of the first measuring beam and the focusing position of the second measuring beam is between 20 μm and 1,000 μm.

10. A computer-readable storage medium storing a program configured to cause a computer to execute the imaging method according to claim 7.

11. A program configured to cause a computer to execute the imaging method according to claim 7.

12. The imaging method according to claim 7, further comprising:

aligning focusing positions of the first measuring beam and the second measuring beam irradiated by the irradiation unit with a base layer of the object under examination; and obtaining images of the object after the focusin positions of the first measuring beam and the second measuring beam are set to different depths.

13. The imaging method according to claim 12, wherein the object is an eye, and wherein the base layer includes at least one of the pigmented epithelial cells layer, the nerve fiber layer, and the photoreceptor inner and outer segment junction.

14. The imaging method according to claim 12, wherein, in the adjusting of the focusing positions, (a) a focusing position of a measuring beam with a short wavelength is adjusted to a depth less than the base layer and (b) a focusing position of a measuring beam with a long wavelength is adjusted to a depth greater than the base layer.

obtaining images of the object after the focusing positions of the first measuring beam and the second measuring beam are set to different depths.

15. The imaging apparatus according to claim 1, further comprising a light emitting unit for emitting a first light beam and a second light beam that differ from each other in a center wavelength in order to irradiate the object with light;

a first splitting unit for splitting the first light beam into a first reference beam and the first measuring beam; and a second splitting unit for splitting the second light beam into a second reference beam and the second measuring beam;

an irradiation unit for irradiating the object under examination with the first measuring beam adjusted by the first adjustment unit and the second measuring beam adjusted by the second adjustment unit;

a first detecting unit for detecting an interference light beam from a first returning light beam and the first reference beam, wherein the first returning light beam results from the first measuring beam reflected or scattered by the object;

a second detecting unit for detecting an interference light beam from a second returning light beam and the second reference beam, wherein the second returning light beam results from the second measuring beam reflected or scattered by the object; and an image acquiring unit for acquiring a tomographic image of the object as the image based on the interference light that is detected.

16. The imaging apparatus according to claim 1, wherein the first adjustment unit controls the focusing position of the first measuring beam by controlling the degree of flux convergence of the first measuring beam and the second adjustment unit controls the focusing position of the second measuring beam by controlling the degree of flux convergence of the second measuring beam.

17. The imaging apparatus according to claim 1, further comprising a dichroic mirror that reflects one of the first measuring beam and the second measuring beam, and transmits the other measuring beam.

18. The imaging apparatus according to claim 1, further comprising a common scanning unit for simultaneously scanning the first measuring beam and the second measuring beam, after passing through the dichroic mirror.

19. An imaging apparatus that acquires an image of an object using a returning light beam from the object by irradiating, with an irradiation unit, the object with a first measuring beam and a second measuring beam that differ from each other in a center wavelength, the imaging apparatus comprising:

a first adjustment unit for adjusting a focusing position of the first measuring beam in a depth direction;

a second adjustment unit for adjusting a focusing position of the second measuring beam in the depth direction; and a controlling unit for controlling, after the focusing position of the first measuring beam and the focusing position of the second measuring beam are adjusted to a predetermined layer of the object, at least one of the first adjustment unit and the second adjustment unit such that the focusing position of the first measuring beam and the focusing position of the second measuring beam are at different positions in the depth direction.

20. The imaging apparatus according to claim 19, further comprising:
an aligning unit for aligning focusing positions of the first measuring beam and the second measuring beam irradiated by the irradiation unit with a base layer of the object under examination; and
an obtaining unit for obtaining images of the object after the focusing positions of the first measuring beam and the second measuring beam are set to different depths.

21. The imaging apparatus according to claim 20, wherein the object is an eye and the base layer includes at least one of the pigmented epithelial cells layer, the nerve fiber layer, and the photoreceptor inner and outer segment junction.

22. The imaging apparatus according to claim 19, wherein a depth of focus of the first measuring beam and a depth of focus of the second measuring beam are continuous or partially overlap in a direction of an optical axis.

23. The imaging apparatus according to claim 19, wherein a distance between the focusing position of the first measuring beam and the focusing position of the second measuring beam is between 20 μm and 1,000 μm.

24. The imaging apparatus according to claim 20, wherein the controlling unit controls a focusing position of a measuring beam with a short wavelength to be adjusted to a depth less than the base layer and a focusing position of a measuring beam with a long wavelength to be adjusted to a depth greater than the base layer.

25. An imaging method that irradiates an object with a first measuring beam and a second measuring beam that differ from each other in a center wavelength, and acquires an image of the object using returning light from the object, the imaging method comprising:
a first adjustment step of adjusting a focusing position of the first measuring beam in a depth direction;
a second adjustment step of adjusting a focusing position of the second measuring beam in the depth direction; and
a controlling step of controlling, after the focusing position of the first measuring beam and the focusing position of the second measuring beam are adjusted to a predetermined layer of the object, at least one of the first adjustment step and the second adjustment step such that the focusing position of the first measuring beam and the focusing position of the second measuring beam are at different positions in the depth direction.

26. The imaging method according to claim 25, further comprising an adjusting step of adjusting a beam diameter of the first measuring beam and a beam diameter of the second measuring beam.

27. The imaging method according to claim 25, further comprising a third adjustment step of adjusting the adjusted focusing positions of the first measuring beam and the second measuring beam, simultaneously.

28. The imaging method according to claim 25, further comprising a light emitting step of emitting a first light beam and a second light beam that differ from each other in a center wavelength in order to irradiate the object with light,
wherein the light emitting step uses a first light source for generating the first light beam and a second light source for generating the second light beam.

29. The imaging method according to claim 25, further comprising a light emitting step of emitting a first light beam and a second light beam that differ from each other in a center wavelength in order to irradiate the object with light,
wherein the light emitting step uses a light source for generating broadband light and a plurality of filters each capable of selecting a single wavelength, and
wherein the plurality of filters is used to generate the first light beam and the second light beam.

30. The imaging method according to claim 25, further comprising:
a light emitting step of emitting a first light beam and a second light beam that differ from each other in a center wavelength in order to irradiate the object with light;
a first splitting step of splitting the first light beam into a first reference beam and the first measuring beam; and
a second splitting step of splitting the second light beam into a second reference beam and the second measuring beam,
wherein an optical path length adjusting unit for the first reference beam and an optical path length adjusting unit for the second reference beam are common.

31. The imaging method according to claim 25, further comprising:
a light emitting step of emitting a first light beam and a second light which beam that differ from each other in a center wavelength in order to irradiate the object with light;
a first splitting step of splitting the first light beam into a first reference beam and the first measuring beam; and
a second splitting step of splitting the second light beam into a second reference beam and the second measuring beam;
an irradiation step of irradiating the object under examination with the first measuring beam adjusted in the first adjustment step and the second measuring beam adjusted in the second adjustment step;
a first detecting step of detecting an interference light beam from a first returning light beam and the first reference beam, wherein the first returning light beam results from the first measuring beam reflected or scattered by the object;
a second detecting step of detecting an interference light beam from a second returning light beam and the second reference beam, wherein the second returning light beam results from the second measuring beam reflected or scattered by the object; and
an image acquiring step of acquiring a tomographic image of the object as the image based on the interference light that is detected.

32. The imaging method according to claim 25, wherein the first adjustment step controls the focusing position of the first measuring beam by controlling the degree of flux convergence of the first measuring beam and the second adjustment step controls the focusing position of the second measuring beam by controlling the degree of flux convergence of the second measuring beam.

* * * * *